United States Patent
Winkler et al.

[11] Patent Number: 5,923,035
[45] Date of Patent: Jul. 13, 1999

[54] INFRARED ABSORPTION MEASURING DEVICE

[75] Inventors: Tobias Winkler, Lübeck; Horst-Dieter Hattendorff, Bad Schwartau, both of Germany

[73] Assignee: Drägerwerk AG, Lübeck, Germany

[21] Appl. No.: 08/915,898

[22] Filed: Aug. 21, 1997

[30] Foreign Application Priority Data

Apr. 4, 1997 [DE] Germany ............................ 197 13 928

[51] Int. Cl.$^6$ ................................................. G01N 21/35
[52] U.S. Cl. .......................... 250/338.5; 250/353; 250/349
[58] Field of Search ............................. 250/338.3, 338.5, 250/345, 346, 349, 353

[56] References Cited

U.S. PATENT DOCUMENTS

| | | | |
|---|---|---|---|
| 5,428,222 | 6/1995 | Alexay | 250/343 |
| 5,451,787 | 9/1995 | Taylor | 250/338.5 |

FOREIGN PATENT DOCUMENTS

| | | | |
|---|---|---|---|
| 195 20 488 C1 | 9/1996 | Germany . | |
| 57-29933 | 2/1982 | Japan | 356/437 |
| 2262338 | 6/1993 | United Kingdom | 250/338.5 |

*Primary Examiner*—Constantine Hannaher
*Assistant Examiner*—Darren M. Jiron
*Attorney, Agent, or Firm*—McGlew and Tuttle, P.C.

[57] ABSTRACT

A measuring device for determining the concentration of gases with two identical radiation sources and two radiation detectors, which delivers stable measured values despite the contamination that occurs or the shielding from radiation of the outer optical surfaces exposed to the gases or to mixtures of gases and despite possible mechanical disadjustments. The two radiation detectors are provided with an optical concentrator each for bundling the radiation, and being arranged in a gas-tight housing together with the two identical radiation sources and with a beam splitter. One radiation source is directed through a window that is transparent to infrared light to a plane mirror outside the gas-tight housing, and the beam path reflected by the plane mirror falls through the window that is transparent to infrared light onto the beam splitter. The beam splitter splits both the radiation of the first radiation source reflected by the plane mirror and that of the second radiation source between two radiation detectors. The first radiation detector is used as a measuring detector and the second radiation detector is used as a reference detector.

6 Claims, 1 Drawing Sheet

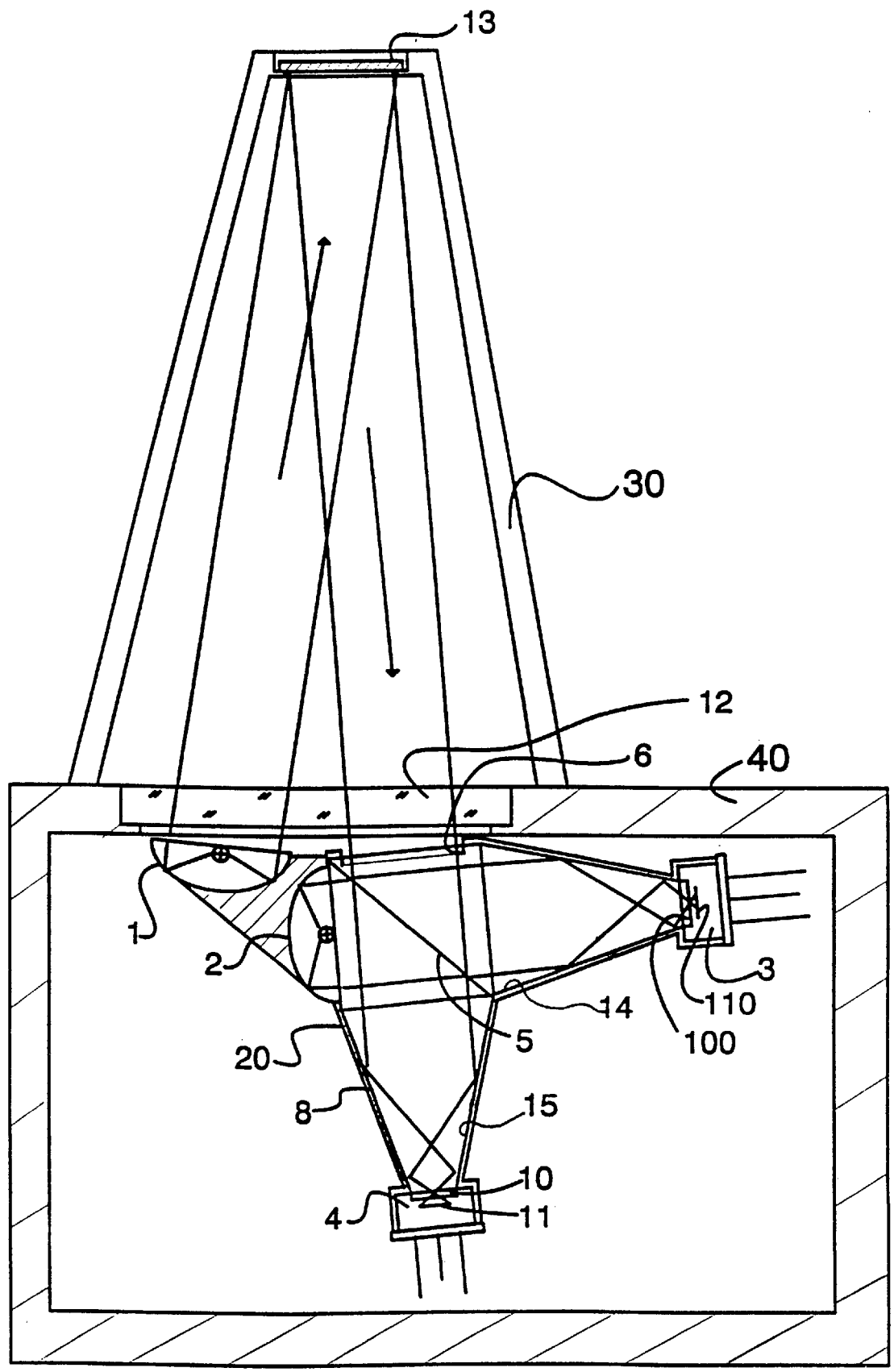

INFRARED ABSORPTION MEASURING DEVICE

FIELD OF THE INVENTION

The present invention pertains to an infrared absorption measuring device for determining the concentration of gases by infrared absorption with two radiation sources and two radiation detectors.

BACKGROUND OF THE INVENTION

A measuring device of this type is shown in German Patent No. DE 195 20 488 C1, in which the gas to be measured flows into a hollow guide, which is used as a measuring section, and wherein the absorption of infrared radiation by the gas to be detected is, in general, an indicator of the concentration of that gas. The drawback of this prior-art measuring device is the fact that the intensity at the site of the radiation-sensitive detectors may become very low depending on the number of curvatures in the hollow guide.

SUMMARY AND OBJECTS OF THE INVENTION

The primary object of the present invention is to provide a measuring device for determining the concentration of gases, especially of explosive gases or gas mixtures, which delivers stable measured values despite the contamination that occurs or the shielding from radiation of the outer optical surfaces exposed to the gases or to mixtures of gases and despite possible mechanical disadjustments.

According to the invention, a measuring device is provided for determining the concentration of gases by infrared absorption. The device includes two radiation sources and two radiation detectors. The two radiation detectors are provided with an optical concentrator each and the detectors are arranged in a gas-tight housing together with two, identical radiation sources and with a beam splitter. One radiation source is directed through a window, that is transparent to infrared light, toward a plane mirror outside the gas-tight housing. The beam path reflected by the plane mirror then falls through the window that is transparent to infrared light onto the beam splitter, which splits both the radiation of the first radiation source reflected by the plane mirror between the two radiation detectors and also the radiation of the second radiation source between the two radiation detectors. The first radiation detector is used as a measuring detector, and the second radiation detector is used as a reference detector.

One essential advantage of the measuring device according to the present invention is that a compact, robust device, which is also suitable for use under extreme conditions, is made available. Measuring devices according to the present invention are typically used in stationary operation at industrial sites to measure toxic and/or explosive gases or vapors in the atmosphere to protect people and facilities. Furthermore, contamination of the optical system by aerosols and dust, varying atmospheric humidities ranging practically from 0% to nearly 100% relative humidity and temperatures ranging from −40° C. to +70° C. occur under the usual conditions of use. In addition, salt crystals are also frequently formed, especially in offshore areas, but protection of the sensitive parts of an optical gas-measuring device by dust filters or diaphragms is undesirable, because the entry of the gas to be measured is also hindered in such cases. Therefore, so-called open measuring systems without sample holder are preferred for these cases of application. The sample holder proper consists here only of the limitations of the front surfaces of the sample holder by an infrared window and mirror without a lateral limitation of the sample holder. The requirement to have a stable, drift- and error-free operation of an optical infrared measuring device over prolonged periods of time of up to several years, which is satisfied by the device of the present invention, is especially important.

It is a further object of the present invention to provide an optical infrared measuring device for determining the concentrations of gases, wherein the measuring path proper is open.

It has been known that two radiation detectors are used in optical gas sensors to compensate measured reductions in the infrared radiation that are not caused by the gas. While the first detector measures only radiation from a wavelength range in which the gas to be detected has an absorption band, the second detector is sensitive only to radiation from an adjacent range of the spectrum, in which range the gas does not absorb. The quotient of these two signals changes only if the gas to be detected is present in the gas-measuring path. Contaminations and other, nonspectral changes of the radiation power should, in general, affect both detectors in the same manner, so that the quotient remains constant in these cases. However, drifts, which are caused by a contamination of the beam path, may also occur in a setup with two detectors. Since contaminations are not distributed homogeneously, in general, over the radiation cross section, the spatial radiation power distribution changes over the cross section of the optical system behind the contaminated optical element. In connection with the remaining asymmetry of the splitting of the radiation between two detectors, this leads to a change in the quotient, i.e., to a drift of the display of the device. The present invention provides a measuring device whose optical arrangement is also insensitive to asymmetric disturbances in the beam path. The measuring device according to the present invention pertains, in particular, to so-called nondispersive infrared analyzers, which have low cross sensitivity to other gases or atmospheric humidity present in the atmosphere being measured due to the use of gas-specific interference filters with band pass characteristic.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a schematic view of the gas sensor according to the invention.

DESCRIPTION OF THE PREFERRED EMBODIMENT

Referring to the only drawing in particular, the design of a measuring device according to the present invention will be explained by means of the only figure based on an exemplary embodiment. The gas sensor being described has a housing 40 with two identical, broad-band thermal radiators, whose radiation is collimated by means of a parabolic mirror each in the entire emitted spectral range. A complete radiation source 1 or 2 comprises here a parabolic mirror and an incandescent lamp. The collimated light beam of the radiation source 1 passes through a gas volume of a predetermined length containing the gas to be measured to subsequently reach a beam splitter 5, behind which two selective radiation detectors 3 and 4 are arranged. An interference filter 100 with band pass characteristics, whose spectral passband is in the range of absorption of the gas to be detected, is located in front of the radiation detector 3. There are no absorption lines either of the gas to be measured or of other gases usually contained in the atmosphere to be measured in the passband of the second interference filter 10, which is arranged in front of the second radiation detector 4. The second radiation source 2 radiates directly, without radiating through the gas volume, into the same beam splitter 5, which also distributes the radiation of the first radiation source 1 between the radiation detectors 3, 4. The modulation of the radiation sources 1, 2 with different frequencies and demodulation of the detector signals by means of lock-in amplifiers makes it possible to assign the different signals occurring at each radiation detector 3 or 4 to the respective radiation source 1 or 2. It is essential for the measuring device according to the present invention that a nonimaging concentrator 14, 15 each is arranged between the beam splitter 5 and each radiation detector 3 or 4. These concentrators 14, 15 bundle the parallel incident light and generate a uniform radiation distribution in the plane of the radiation-sensitive detector crystal 110, 11. Depending on the specifications of the special beam path and/or the mechanical space available in the particular device, the concentrators 14, 15 may have a defined conical or parabolic profile or be designed in the form of a CPC (Compound Parabolic Concentrator). The inner surface 8 of the concentrators 14, 15 is designed as a highly reflecting surface. In a prior-art beam splitter design, the detectors are not irradiated with exactly the same spatial intensity distributions because of mechanical tolerances, inhomogeneities in the beam profile and the existing divergence of the beam. Therefore, a change in the spatial intensity distribution due to asymmetric contamination of the beam path also has different effects on the detectors, and it leads to an undesired change in the quotient of the measured signal and reference signal and to a drift in the display of the gas-measuring device. The spatial intensity distribution at the site of the radiation detector 3 and 4 is mixed and smoothed and the radiation power present in the entry aperture of the concentrator 14 and 15 is concentrated to the detector crystal 110 and 11 directly behind the exit aperture of the concentrator 14 and 15 due to the use of nonimaging concentrators 14, 15. It is important that the beams entering the concentrators 14, 15 are not reflected from the concentrators 14, 15 opposite their original direction. A conical concentrator 14 and 15 consequently has an optimal length, and an exceeding of this length at constant cone angle does not lead to a further increase in the optical efficiency. The best results were obtained with concentrators 14, 15 which have an entry aperture with a diameter of 15 mm, an opening angle of 14°, a length of 20 mm, as well as an exit aperture with a diameter of 5 mm, and the size of the entry aperture is adapted to the cross section of the incident light bundle used, and is, in particular, equal to same. The light bundle has this cross section in order to be insensitive to individual drops and dust particles, which may settle on the outer optical surfaces (plane mirror 13 fixed by struts 30 as well as window 12 transparent to infrared light). The opening angle is adjusted to the angle of the field of view of the radiation detectors 3, 4 used. Typically this angle is 60° for pyroelectric detectors, which are preferably used. An incident light beam, which is parallel to the optical axis and falls on the mirrored surface 8 in the front part of the concentrator 14 or 15, has a maximum angle of $4\times14°=56°$ against the optical axis after two reflections in the concentrator 14 or 15. In the case of more than two reflections of the entering light beams in the concentrators 14, 15, the angle formed with the optical axis of the optical concentrator 14 or 15 is greater than 90°, depending on the opening or cone angle of the concentrators 14, 15, as a consequence of which the beam is reflected from the concentrator 14 or 15 opposite its original direction, in the direction of incidence. A conical concentrator 14 or 15 consequently has an optimal length, whose exceeding at constant cone angle does not lead to a further increase in the efficiency of the optical intensity. The measuring device according to the present invention, which is explained by means of the figure, is independent from asymmetric disturbances in radiation if the total radiation reflected or transmitted by the beam splitter 5 is radiated into the corresponding concentrator 14 or 15 and if the intensity maximum behind the concentrator 14 or 15 is completely bundled onto the detector crystal 11 or 110 and if the intensity distribution in the plane of the detector displays the most uniform possible, locally unstructured reduction in intensity in the case of an asymmetric disturbance of the beam path. A geometrically nonuniform beam splitting, when, e.g., 50% of the intensity is radiated into the concentrator 14 or 15, but only 40% into the other because of mechanical disadjustment, could cause a symmetric radiation disturbances to also affect the quotient of the measured radiation intensities. The parallel incident beam bundle is limited by the diaphragm 6 in front of the beam splitter 5 to the extent that it falls completely into the concentrator 14 and 15 despite minor disadjustments of the beam path, e.g., due to mechanical tolerances, and despite the residual divergence of the bundle. The fact that a nonimaging optical system is used to bundle the intensity in the detector plane is important and advantageous in the object of the present invention. The consequence of this property is that measuring devices according to the present invention are markedly more insensitive to mechanical disadjustments of the beam path. Thus, mass-produced products are also considerably less expensive, because they can be made optically more insensitive. The radiation sources 1, 2, and the optical concentrators 14, 15 include reflectors that are preferably prepared as a uniform injection-molded plastic part with a reflective coating on at least one surface. Another advantage of the arrangement according to the present invention arises from the nonimaging optical system in relation to the exact position of the beam splitter 5. Thus, a tilting of a parabolic reflector would lead only to a displacement of a slightly structured light reflection in the entry aperture of the beam splitter housing. However, this effect is obviously not linked with any great signal losses or structural changes in the detector plane (no shifting of an image). The bundling of the radiation to the detectors is performed in the optical system according to the present invention only at the end of the beam path by means of the concentrators 14, 15. In summary, an infrared optical measuring device for determining the concentration of gases is proposed, whose optical system is also insensitive to asymmetric disturbances in the beam path and which maintains the advantages of the use of a measuring and reference detector with two radiation sources for compensating temperature drifts and aging effects.

While a specific embodiment of the invention has been shown and described in detail to illustrate the application of the principles of the invention, it will be understood that the invention may be embodied otherwise without departing from such principles.

What is claimed is:

1. A measuring device for determining the concentration of gases by infrared absorption, comprising:

a radiation source;

another radiation source substantially identical to said radiation source;

a radiation detector;

another radiation detector;

an optical concentrator provided with said radiation detector;

another optical concentrator provided with said another radiation detector;

a gas-tight housing, said radiation source, said another radiation source, said radiation detector and said another radiation detector being disposed in said gas-tight housing, said gas-tight housing including a window that is transparent to infrared light;

a beam splitter disposed in said gas-tight housing;

a plane mirror disposed outside said gas-tight housing, said radiation source being directed through said window that is transparent to infrared light toward said plane mirror outside said gas-tight housing to provide a beam path reflected by said plane mirror, said beam path reflected by said plane mirror passing through said window that is transparent to infrared light onto said beam splitter, said another radiation source being directed to said beam splitter, said beam splitter splitting radiation of said radiation source reflected by said plane mirror between said radiation detector and said another radiation detector and said beam splitter splitting radiation of said another radiation source between said radiation detector and said another radiation detector, and wherein said radiation detector is a measuring detector, and said another radiation detector is a reference detector.

2. The measuring device in accordance with claim 1, wherein said optical concentrator and said another optical concentrator have an opening angle of 14°, a length of 20 mm, an entry aperture with a diameter of 15 mm, and an exit aperture with a diameter of 5 mm.

3. The measuring device in accordance with claim 1, wherein said radiation source, said another radiation source, said optical concentrator and said another optical concentrator include reflectors prepared as a uniform injection-molded plastic part with a reflecting coating on at least one surface.

4. The measuring device in accordance with claim 1, wherein said radiation detector is provided with an interference filter and said another radiation detector is provided with another interference filter and each with a detector crystal, wherein said interference filter has a band pass characteristic with a spectral passband in the range of absorption of the gas or gases to be detected, and wherein there are no gas absorption lines in the passband of said another interference filter.

5. The measuring device in accordance with claim 4, wherein said detector crystal is pyroelectric.

6. The measuring device in accordance with claim 1, wherein:

said optical concentrator and said another optical concentrator are nonimaging concentrators.

* * * * *